United States Patent
Adler et al.

(10) Patent No.: US 11,847,721 B2
(45) Date of Patent: Dec. 19, 2023

(54) ANALYSIS OF MEDICAL IMAGES

(71) Applicant: Elekta AB (publ), Stockholm (SE)

(72) Inventors: Jonas Anders Adler, Stockholm (SE); Ozan Öktem, Sundbyberg (SE)

(73) Assignee: ELEKTA AB (PUBL), Stockholm (SE)

(*) Notice: Subject to any disclaimer, the term of this patent is extended or adjusted under 35 U.S.C. 154(b) by 0 days.

(21) Appl. No.: 16/623,660

(22) PCT Filed: Jun. 21, 2018

(86) PCT No.: PCT/EP2018/066663
§ 371 (c)(1),
(2) Date: Dec. 17, 2019

(87) PCT Pub. No.: WO2018/234503
PCT Pub. Date: Dec. 27, 2018

(65) Prior Publication Data
US 2021/0150780 A1      May 20, 2021

(30) Foreign Application Priority Data
Jun. 21, 2017   (EP) ..................................... 17177068

(51) Int. Cl.
*G06T 11/00*      (2006.01)
*G16H 30/00*     (2018.01)

(52) U.S. Cl.
CPC .......... *G06T 11/006* (2013.01); *G06T 11/005* (2013.01); *G06T 11/008* (2013.01);
(Continued)

(58) Field of Classification Search
CPC .................................................... G06T 11/006
See application file for complete search history.

(56) References Cited

U.S. PATENT DOCUMENTS

| | | | |
|---|---|---|---|
| 9,140,803 B2* | 9/2015 | Bertram | A61B 6/032 |
| 9,232,928 B2* | 1/2016 | Mostafavi | A61N 5/1049 |

(Continued)

FOREIGN PATENT DOCUMENTS

| | | |
|---|---|---|
| WO | WO-2013188957 A1 | 12/2013 |
| WO | WO-2015103184 A1 | 7/2015 |

OTHER PUBLICATIONS

"International Application Serial No. PCT/EP2018/066663, International Search Report dated Sep. 3, 18", (dated Sep. 3, 2018), 3 pgs.

(Continued)

*Primary Examiner* — Oneal R Mistry
(74) *Attorney, Agent, or Firm* — Schwegman Lundberg & Woessner, P.A.

(57) ABSTRACT

Much of the image processing that is applied to medical images is a form of "inverse problem". This is a class of mathematical problems in which a "forward" model by which a signal is converted into dataset is known, to at least some degree, but where the aim is to reconstruct the signal given the resulting dataset. Thus, an inverse problem is essentially seeking to discover x given knowledge of A(x)+noise by finding an appropriate reconstruction operator $A^\dagger$ such that $A^\dagger(A(x)+\text{noise}) \approx x$, thereby enabling us to obtain x (or a close approximation) given knowledge of an output dataset consisting of A(x)+noise. Generally, several such processes (or their equivalents) are applied to the image dataset. If the first process (for example, noise reduction) is expressed via a first reconstruction operator $A_1^\dagger$ characterised by a parameter set $\Theta_1$ and the second process (for example, segmentation) is expressed via a second reconstruction operator $A_2^\dagger$ characterised by a parameter set $\Theta_2$, then the result of the two steps applied consecutively is $A_2^\dagger(A_1^\dagger(y))$. This can be expressed as an overall reconstruction operator $P^+$, characterised by a parameter set $\Phi$. If we then (Continued)

allow a machine learning process to optimise $P^+$, then the steps previously carried out separately can be combined into a single optimisation. This yields advantages in terms of computational load and in the accuracy of the end result.

7 Claims, 3 Drawing Sheets

(52) U.S. Cl.
CPC ......... *G16H 30/00* (2018.01); *G06T 2210/41* (2013.01); *G06T 2211/424* (2013.01)

(56) References Cited

U.S. PATENT DOCUMENTS

| | | | |
|---|---|---|---|
| 2007/0071169 A1* | 3/2007 | Yeo | A61N 5/1031 |
| | | | 378/65 |
| 2008/0240533 A1 | 10/2008 | Piron et al. | |
| 2016/0193482 A1* | 7/2016 | Fahrig | H05H 9/048 |
| | | | 600/1 |
| 2017/0055931 A1* | 3/2017 | Paysan | G06T 11/008 |
| 2018/0249979 A1* | 9/2018 | Wang | A61B 5/055 |

OTHER PUBLICATIONS

"International Application Serial No. PCT/EP2018/066663, Written Opinion dated Sep. 3, 2018", (dated Sep. 3, 2018), 6 pgs.

\* cited by examiner

ANALYSIS OF MEDICAL IMAGES

PRIORITY APPLICATIONS

This application is a U.S. National Stage Filing under 35 U.S.C. 371 from International Application No. PCT/EP2018/066663, filed on Jun. 21, 2018, and published as WO2018/234503 on Dec. 27, 2018, which claims the benefit of priority to European Application No. 17177068.8, filed on Jun. 21, 2017; the benefit of priority of each of which is hereby claimed herein, and which applications and publication are hereby incorporated herein by reference in their entirety.

FIELD OF THE INVENTION

The present invention relates to the analysis of medical images, such as for use in radiotherapy.

BACKGROUND ART

Medical imaging is an established field, with the aim of deriving information as to the internal structure of the patient's body by observing its effect on an incident signal and making an inference as to what structure must have been present in order to yield that effect.

Various imaging modalities are known at present. X-ray imaging methods observe the attenuation of x-rays after passing through the body, and CT reconstruction is a technique for inferring a three-dimensional structure for the patient based on a plurality of x-ray projections taken from different directions. MRI systems look at the reaction of atomic nuclei in the body to an incident radio-frequency signal when in a magnetic field, and (likewise) infer a three-dimensional structure from this. Ultrasound techniques detect the reflection of high-frequency vibrations by discontinuities in the body and, from this, infer a three-dimensional structure.

These medical images can be used for a variety of purposes. Originally, they were observed by a clinician and a diagnosis was made based on the image. Such images have also been used to plan treatments such as radiotherapy, by identifying the location, shape and size of a tumour or other lesion and thus allowing a dose to be prescribed. Treatment planning is now largely automated, using an iterative process taking a medical image, a prescribed dose pattern, and a set of apparatus constraints as inputs and yielding (as an output) a sequence of deliverable treatment steps that will achieve that dose pattern.

The results that can be achieved using medical imaging are of course limited by the quality of that image. To this end, work has been directed at both improving the quality of imaging systems and also at enhancing medical images once they have been produced, with a view to eliminating characteristic patterns of noise in the image, or characteristic distortions and artefacts. The specific type of image imperfection is dependent on the imaging modality in question, for example x-ray images suffer from scatter noise and cone-beam CT images can suffer from cupping artefacts. Modality-specific algorithms have therefore been developed which seek to remove these imperfections and produce an image that is more "true", i.e. a more accurate representation of the patient. The enhanced image is then used as the basis for treatment planning (etc).

SUMMARY OF THE INVENTION

Image enhancement of the type described above is a form of "inverse problem". This is a class of mathematical problems in which a "forward" model by which a signal is converted into dataset is known, to at least some degree, but where the aim is to reconstruct the signal given the resulting dataset. Thus, an inverse problem is essentially seeking to discover x given knowledge of $A(x)$+noise by finding an appropriate reconstruction operator $A^\dagger$ such that $$A^\dagger(A(x)+\text{noise}) \approx x$$

thereby enabling us to obtain x (or a close approximation) given knowledge of an output dataset consisting of $A(x)$+noise.

This has been approached with a wide range of methods, including direct inversion (such as filtered back-projection), iterative methods (Algebraic Reconstruction Techniques and Simultaneous Algebraic Reconstruction Techniques) and variational methods. Machine learning techniques have also been applied to the problem more recently.

Reconstruction of the three-dimensional CT or MRI image given the raw attenuation or Fourier transform data are also examples of inverse problems. The dataset outputted by the imaging process is known, but this is the result of applying a process to the unknown patient structure. The problem is to derive the structure that must have been responsible for producing the resulting dataset—an example of an inverse problem.

The processes that are applied to the final version of the image, i.e. the image after reconstruction and enhancement, are also examples of inverse problems. For example, the process of image segmentation seeks to classify the 3D image dataset in order to identify different tissue types, and is thus seeking to infer what deeper (tissue-specific) level of patient structure which would have resulted in the 3D image. Alternatively, treatment planning works from the desired end result, a three-dimensional dose prescription, and seeks to discover what sequence of treatment steps would, if applied using the defined apparatus to a patient having the structure shown in the segmented image, have resulted in that three-dimensional dose distribution.

At present, therefore, the process that is adopted consists of the solution of several inverse problems in sequence, such as image reconstruction, followed by image enhancement, followed by tissue segmentation, followed by treatment planning. This is non-optimal—partly due to the sheer volume of computation, but mainly because each step involves a process that aims for a specific type or quality of image. For example, image enhancement techniques aim to yield an image that looks to a radiologist like a perfect artefact-free image "should" look. This may or may not be an optimal starting point for the next process in the sequence.

The present invention therefore provides (in one aspect) a medical image analysis apparatus comprising a data store for receiving output data of a medical imaging apparatus, and a processing unit programmed to iteratively optimise a single inverse function that is arranged to output at least one of a segmented image dataset and a treatment plan when applied to the stored output data. The output data can be the raw unreconstructed data, such as the projection images of a CT scanning apparatus or the Fourier transform data of a magnetic resonance imaging apparatus, or it can be the reconstructed volume image.

Other intermediate steps can be combined, and thus in another aspect the present invention provides a medical image analysis apparatus comprising a data store for receiving unsegmented output data of a medical imaging apparatus, and a processing unit programmed to iteratively optimise a single inverse function that is arranged to output a treatment plan when applied to the stored output data. In this case, the output data can be an image produced by one of a CT or MRI scanner which has been filtered to reduce at least one of image noise and image artefacts, or data from an earlier stage of processing.

Alternatively, in a third aspect the present invention provides a medical image analysis apparatus comprising a data store for receiving unreconstructed output data of a medical imaging apparatus, and a processing unit programmed to iteratively optimise a single inverse function that, when applied to the stored raw unreconstructed output data, is arranged to produce a reconstructed volume image in which image noise and/or artefacts have been alleviated.

In this application, we use the term "image" to indicate a dataset that is representative of the internal structure of a patient. That dataset may or may not be presented in a viewable format such as (for example) a bitmap image file. As an alternative, it may be stored as a dataset containing the information in an alternative format, perhaps one that is native to the system that produced it, such as a series of x-ray attenuation coefficients, or one that is suited to the subsequent processing steps such as treatment planning. The dataset may be presentable in a viewable format, but it is not essential to the invention that it is ever so presented.

Likewise, we use the term "segmentation" to refer to a division of the image dataset into meaningful subdivisions. These subdivisions can be structural, such as the identification of regions of the image that represent specific organs such as the liver, kidneys, lungs, heart, spinal cord, prostate, intestines etc. Alternatively (or in addition), they can be functional subdivisions, such as the identification of lesions as opposed to healthy tissue and/or the identification of sensitive tissues (for example the spinal cord, intestines, optic nerve and the like) into which dosage should be minimised as opposed to other generic tissue types.

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
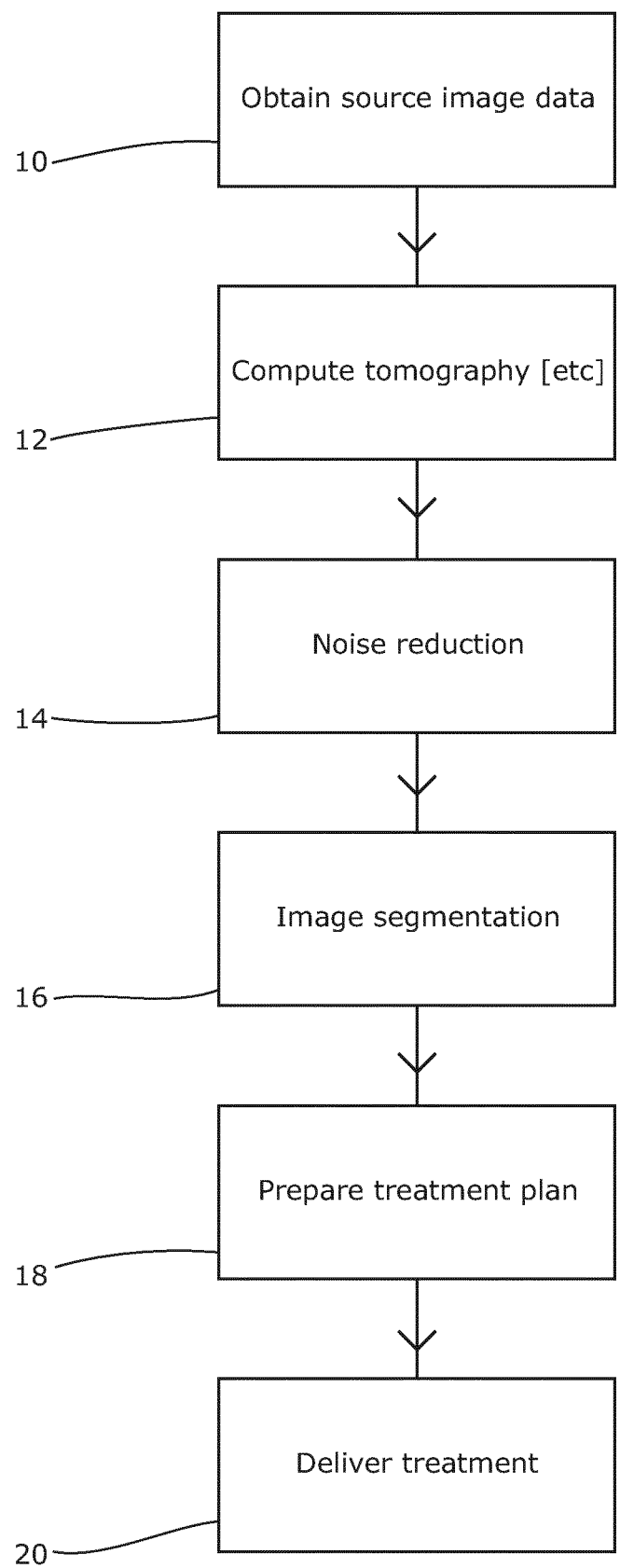
FIG. 1 is a flowchart illustrating the process flow of a conventional apparatus according to the present invention.

Referring to FIG. 1, this shows the usual process flow that is adopted for imaging data used for medical purposes. The first step is to scan the patient using whatever imaging modality is available and most appropriate, such as a CT scanner, MRI scanner or ultrasound scanner (step 10). The raw data thus obtained then needs to be converted to a 3D or tomographic image via a mathematical process (step 12), with different techniques being applicable dependent on the modality concerned. For example, CT scanners produce a series of projection images, usually 1- or 2-dimensional, from a variety of angles which are then reconstructed to yield a volume image. MRI scanners output a series of Fourier coefficients which are likewise reconstructed into a volume image. Ultrasound systems produce echo responses which are either assembled into a two-dimensional image or reconstructed into a three-dimensional image.

This image dataset will usually contain noise and/or image artefacts, so it is passed through a filter process (step 14) to remove these and make the image easier for a radiologist to interpret. Filters are selected based on the imaging modality, such as a low-pass filter to reduce scatter noise in a CT image, and a cup filter to reduce image hardening artefacts from cone-beam CT images. With a clean image (or, rather, a cleaner image) thus obtained, a segmented image can be prepared by identifying regions within the image that correspond to structures of relevance to the subsequent treatment, such as tumours or other lesions to be treated, organs that are at risk from high doses, bony structures that will affect the x-ray transmission characteristics of the patient, etc. Segmentation has historically been carried out by clinicians, but software tools for automatic segmentation have become available in recent times.

One or more of these steps may be omitted in particular circumstances. Equally, other processes may also be included where relevant and/or necessary, in addition to the above steps, instead of one or more steps, or as part of one or more steps. For example, co-registration processes correct the spatial referencing of an image (2D or 3D) in order to match another reference frame, for example a fixed frame of reference in the room, or the frame of reference of another image also being used for the same purposes, or the frame of reference of another image that was used previously, such as for diagnosis or for determining the dose distribution.

The segmented image can then be used to prepare a treatment plan (step 18). This is a dataset which includes a sequence of instructions for the radiotherapy apparatus, typically a set of beam shapes to emit from specific angles for specific times at specific doses. When delivered by the radiotherapy apparatus (step 20), these individual beam segments then add up to form the three-dimensional dose distribution called for by the clinician. Alternatively, the segmented image may be used for other purposes such as diagnosis and dose calculation, either manually or via an automated process.

All of the above steps are (as discussed above) inverse problems, i.e. problems in which the challenge is to work out the initial dataset which, when subjected to a process with known parameters, results in the observed dataset. For example, the characteristics of both the deterministic and the random aspects of x-ray transmission through tissue are generally well characterised, and the structure and capabilities of CT scanning and radiotherapy apparatus are known. Thus, the processes by which an a priori known patient structure is converted into projection images is well characterised. Similarly, the processes by which a known treatment plan applied to a known patient structure by a known radiotherapy apparatus leads to a resulting dose distribution within the patient is likewise well characterised. However, the problem is to work in the opposite direction, establishing the patient structure if given the projection images, and/or a treatment plan if given a patient structure, a set of machine parameters, and a desired dose distribution.

This is usually obtained by an iterative process. If we denote the "forward" operator as $A_F(x_{actual})$ such that the result $y_{observed}$ is obtained as $y_{observed} = A_F(x_{actual}) + noise$, then in the above examples we know $y_{observed}$ and $A_F$, but need to determine $x_{actual}$. Starting with a candidate $x_i$, we can establish the $y_i$ that results in by applying $A_F$ to $x_i$. This will not generally be equal to $y_{observed}$, so we can calculate an error value such as $(|y_{observed} - y_i|)^2$. By varying the parameters of $x_i$ and recalculating, we can establish a local gradient in the error value, which informs us of the appropriate direction in which to continue varying $x_i$. Eventually we will reach a minimum in the error value, at which point the iteration is declared complete. Other routes to a solution do exist, though.

This can be expressed in alternative mathematical form as a reconstruction operator $A^\dagger$ such that if $y=A_F(x)$ then $A^\dagger(y) \approx x$. Then, the problem becomes one of determining $A^\dagger$; generally this will be characterised by a parameter set $\Theta$ (i.e. the relevant convolutions which when applied to y yield x) which can be determined by a machine learning optimisation process. An example can be found in the paper "Solving ill-posed inverse problems using iterative deep neural networks" by Adler and Öktem at https://arxiv.org/abs/1704.04058.

However, when expressed in this way, the consecutive application of two such processes can be simplified. If the first process (for example, noise reduction) is expressed via a first reconstruction operator $A_1^\dagger$ characterised by a parameter set $\Theta_1$, and the second process (for example, segmentation) is expressed via a second reconstruction operator $A_2^\dagger$ characterised by a parameter set $\Theta_2$, then the result of the two steps applied consecutively is $A_2^\dagger(A_1^\dagger(y))$. This can be expressed as an overall reconstruction operator $P^+$, characterised by a parameter set $\phi$. If we then allow a machine learning process to optimise $P^+$, then there are several results.

First, there may be parameters within the sets $\Theta_1$, $\Theta_2$ which are superfluous to the combined process. If so, then $\phi$ will be less complex than $\Theta_1+\Theta_2$. This is apparent since the trivial solution for $P^+(y)$ is $A_2^\dagger(A_1^\dagger(y))$, so $\phi$ cannot be more complex than $\Theta_1+\Theta_2$. Therefore, the combined operator $P^+$ must be either less complex to determine than both $A_1^\dagger$ and $A_2^\dagger$ combined, or no more complex than the combination.

Second, it is to be expected that the combined operator will yield a more optimised result for the combined steps. This is because a machine-learning-based optimisation process needs to be guided as to what type of result is expected; therefore in the above example the image noise reduction process will aim to provide a visually clean image that is easily interpretable by a radiologist. This may or may not be the ideal starting point for a segmentation process that is carried out by a machine learning process instead. There is no strong reason to expect that it is an ideal starting point, and it might reasonably be expected that the noise reduction processes might eliminate small details that could assist in the segmentation process.

So by combining both steps into a single optimisation process, the process is at least as efficient as individual steps and should be more efficient, but will yield a more optimal final result.

Figure 2:
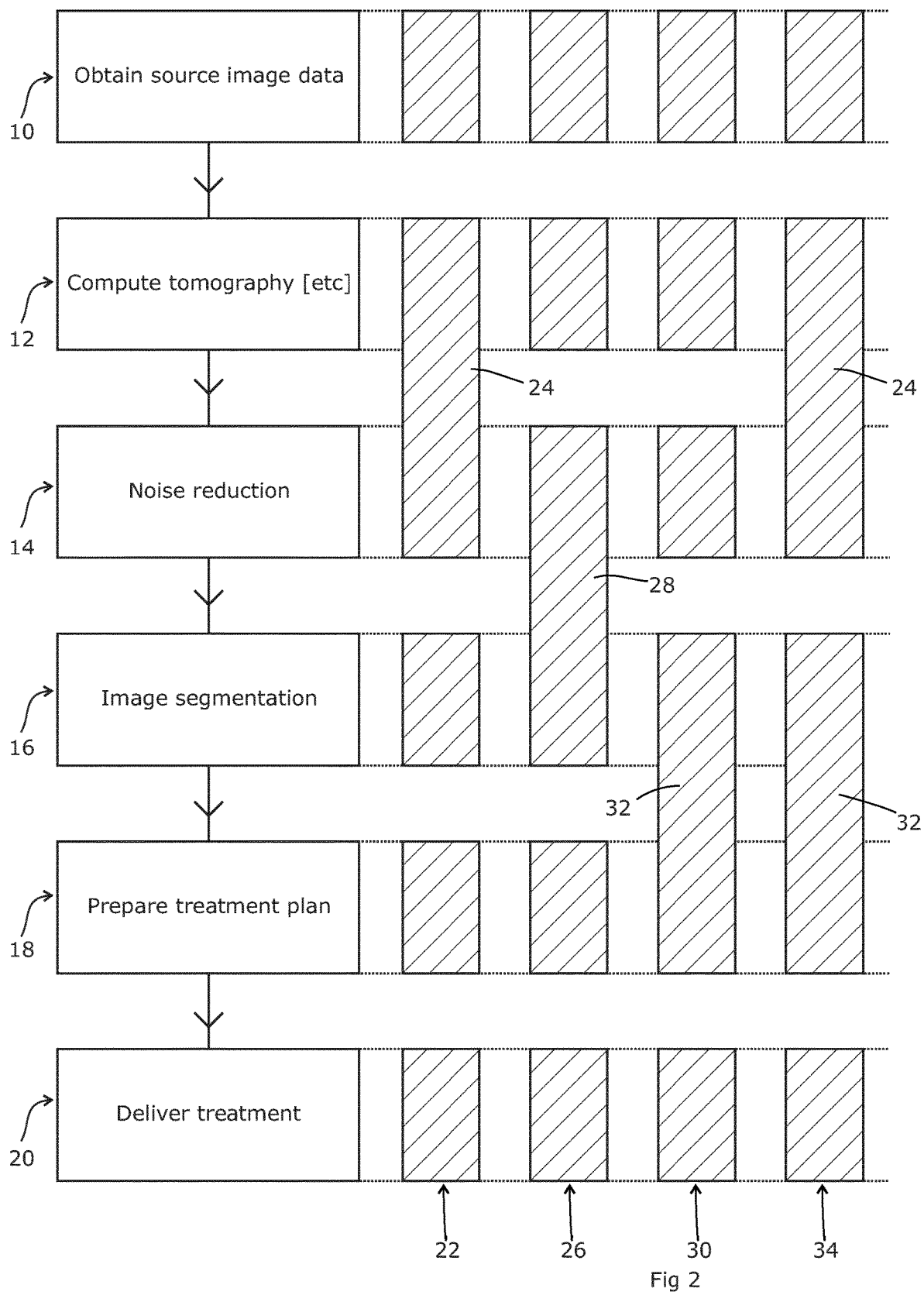
FIGS. 2 and 3 illustrate the schematic process flows of alternative forms of the invention.

FIG. 2 shows a range of possible two-step consolidations according to the above approach. The individual steps 10, 12, 14, 16, 18, 20 of FIG. 1 are shown, and process route 22 shows that step 10 (obtain the source image data) is carried out, followed by a combination of steps 12 and 14 into a single optimisation process 24 that yields a cleaned volume image. That image can then be used (as in FIG. 1) for segmentation 16 and treatment planning 18, before delivery of the treatment at step 20.

As an alternative, process route 26 includes a discrete step 12 of computing the volume image, followed by a combined step 28 consisting of a single optimisation of the noise reduction step 14 and the image segmentation step 16. The clean segmented image can then be used in a treatment planning process 18 before the treatment is delivered at step 20.

A further alternative process route 30 instead combines the segmentation and treatment planning processes into a single step 32. This, this route follows the steps of image acquisition 10, computation of a volume image 12, noise reduction 14, segmentation and treatment planning 32, and treatment delivery 20. Routes 22 and 30 could of course be combined, to produce a route 34 consisting of image acquisition 10, combined computation of a volume image and noise reduction 24, segmentation and treatment planning 32, and treatment delivery 20.

Figure 3:
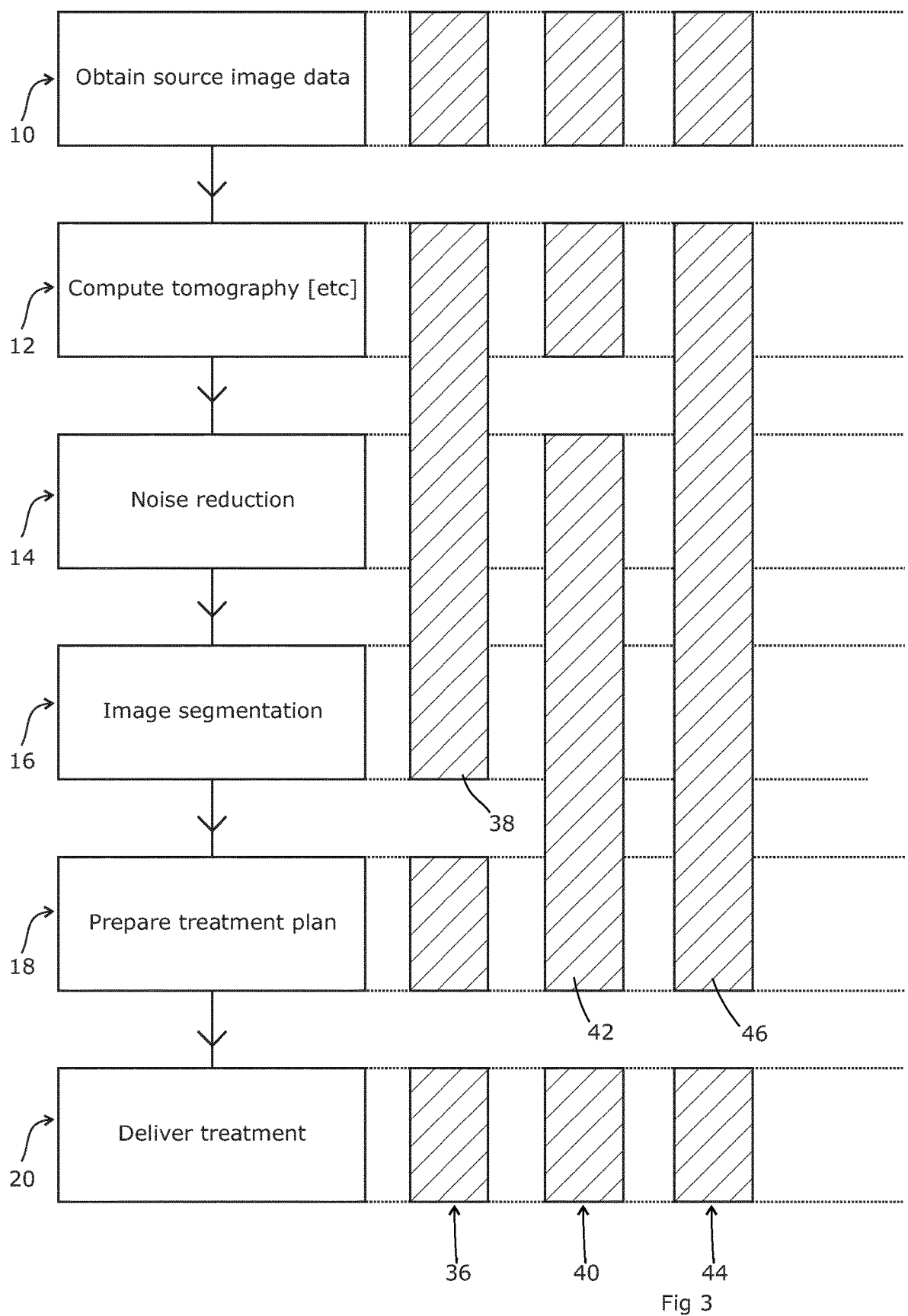

FIG. 3 shows process routes for more aggressive combinations of steps. Thus, process route 36 involves the steps of image acquisition 10, then a combined step 38 of computation of a volume image, noise reduction, and segmentation. This is followed by a treatment planning step 18 and treatment delivery 20. Alternatively, process route 40 involves the steps of image acquisition 10, then the step of computation of a volume image 12, followed by a single combined step of noise reduction, segmentation and treatment planning 42, and then a treatment delivery step 20.

Finally, process route 44 shows an initial step of image acquisition 10, followed by a single optimised computation step that starts with the raw image output of the imaging modality and leads to a deliverable treatment plan which is then delivered in a final step 20. In practice, routes that integrate a larger number of steps into a single optimised process may require a greater computation resource for a given image resolution, as the larger parameter set $\phi$ will call for a correspondingly greater number of dimensions in the computational space. Thus, routes 22, 26, 30, 34 may be preferable in the shorter term in terms of their balance between the resolution available and the computational resources needed. However, the principle still applies to higher levels of integration.

Of course, the intermediate steps may be produced in addition or in parallel to the final output. For example, the reconstructed volume image (processed or otherwise) can be provided as well as the segmented image and/or the treatment plan.

Another inverse problem to which the above process can be applied is that of automated diagnosis. Provided with a clean image, which may be segmented as noted above, the system seeks to identify what disease or abnormality results in the features present in the image. This is therefore an inverse process and could be substituted for the treatment planning step illustrated in the figures. In the manner described above, it could then be integrated with some or all of the volume image computation, noise reduction, and segmentation steps to produce a proposed diagnosis for review by a physician.

It will of course be understood that many variations may be made to the above-described embodiment without departing from the scope of the present invention.

The invention claimed is:

1. A medical image analysis apparatus, comprising:
  a data store for receiving unsegmented output data of a medical imaging apparatus used for imaging a patient, wherein the output data comprises a patient structure prior to delivery of a radiation therapy dose to the patient; and
  a processing unit programmed to compute, before delivery of the radiation therapy dose, a single inverse function that is arranged to:
  when applied to the output data, output a data set comprising:
    a treatment plan for administering the radiation therapy dose to the patient by using the single inverse function to concurrently solve at least two inverse problems including image segmentation and treatment planning.

2. The medical image analysis apparatus according to claim 1, wherein the output data is an image produced by one of a CT or an MRI scanner which has been pre-processed to reduce at least one of image noise and one or more image artefacts.

3. A medical image analysis apparatus, comprising:
a data store for receiving raw unreconstructed output data of a medical imaging apparatus used for imaging a patient, wherein the output data is obtained prior to delivery of a radiation therapy dose to the patient; and
a processing unit programmed to compute, before delivery of the radiation therapy dose, a single inverse function that, when applied to the raw unreconstructed output data, is arranged to:
produce a data set comprising a reconstructed volume image of a patient structure prior to delivery of the radiation therapy dose by using the single inverse function to concurrently solve at least two inverse problems including (a) volume reconstruction and (b) image noise and/or artefact reduction.

4. The medical image analysis apparatus according to claim 3, wherein the raw unreconstructed output data includes at least one of projection images of a CT scanning apparatus or Fourier transform data of a magnetic resonance imaging apparatus.

5. The medical image analysis according to claim 1, wherein computing a single inverse function comprises an iterative optimisation process.

6. The medical image analysis according to claim 3, wherein computing a single inverse function comprises an iterative optimisation process.

7. The medical image analysis apparatus according to claim 1, wherein the data set includes a sequence of instructions for a radiotherapy apparatus, wherein the instructions are a set of beam segments to emit from the radiotherapy apparatus, and wherein the beam segments combine to form a three-dimensional dose distribution.

* * * * *